US010716333B2

(12) United States Patent
Reevell

(10) Patent No.: US 10,716,333 B2
(45) Date of Patent: Jul. 21, 2020

(54) AEROSOL-GENERATING SYSTEM HAVING A CARTRIDGE AND A BYPASS AIR INLET

(71) Applicant: Tony Reevell, London (GB)

(72) Inventor: Tony Reevell, London (GB)

(73) Assignee: Altria Client Services LLC, Richmond, VA (US)

( * ) Notice: Subject to any disclaimer, the term of this patent is extended or adjusted under 35 U.S.C. 154(b) by 223 days.

(21) Appl. No.: 15/838,829

(22) Filed: Dec. 12, 2017

(65) Prior Publication Data

US 2018/0168228 A1 Jun. 21, 2018

Related U.S. Application Data

(63) Continuation of application No. PCT/EP2017/080862, filed on Nov. 29, 2017.

(30) Foreign Application Priority Data

Dec. 19, 2016 (EP) .................................... 16205103

(51) Int. Cl.
*A24F 47/00* (2020.01)
*A24B 15/167* (2020.01)
(Continued)

(52) U.S. Cl.
CPC .......... *A24F 47/008* (2013.01); *A24B 15/167* (2016.11); *A61M 11/042* (2014.02);
(Continued)

(58) Field of Classification Search
CPC ...... A24F 47/00; A24F 47/002; A24F 47/008; A61M 15/06; A61M 15/002;
(Continued)

(56) References Cited

U.S. PATENT DOCUMENTS

2008/0092912 A1* 4/2008 Robinson ............. A24B 15/167
131/200
2013/0014772 A1 1/2013 Liu
(Continued)

FOREIGN PATENT DOCUMENTS

EP          2891415 A2    7/2015
WO   WO-2014110119 A1    7/2014
(Continued)

OTHER PUBLICATIONS

International Preliminary Report on Patentability for corresponding Application No. PCT/EP2017/080862, dated Jun. 25, 2019.
(Continued)

*Primary Examiner* — Timothy A Stanis
*Assistant Examiner* — Cana A Gallegos
(74) *Attorney, Agent, or Firm* — Harness, Dickey & Pierce, P.L.C.

(57) ABSTRACT

An aerosol-generating system(includes a cartridge, a liquid aerosol-forming substrate, and an aerosol-generating device. The cartridge includes a cartridge housing and a solid aerosol-forming substrate. The aerosol-generating device includes a cavity configured to receive at least a portion of the cartridge, an airflow inlet, and an airflow sensor. The airflow sensor is in fluid communication with the airflow inlet and the cavity). The aerosol-generating device includes a bypass air inlet in fluid communication with the cavity, an electric heater configured to heat the liquid aerosol-forming substrate, a power supply, and a controller. The aerosol-generating system is configured so that the cartridge housing substantially prevents airflow through the bypass air inlet when the cartridge is received within the cavity.

15 Claims, 4 Drawing Sheets

(51) Int. Cl.
*A61M 15/06* (2006.01)
*A61M 11/04* (2006.01)
*A61M 15/00* (2006.01)
*A61M 16/00* (2006.01)

(52) U.S. Cl.
CPC ............ *A61M 15/06* (2013.01); *A61M 15/002* (2014.02); *A61M 15/0035* (2014.02); *A61M 2016/0024* (2013.01); *A61M 2016/0039* (2013.01); *A61M 2205/276* (2013.01); *A61M 2205/8206* (2013.01)

(58) Field of Classification Search
CPC ............ A61M 15/0035; A61M 11/041; A61M 11/042; A24B 15/167
See application file for complete search history.

(56) References Cited

U.S. PATENT DOCUMENTS

| | | |
|---|---|---|
| 2013/0333700 A1 | 12/2013 | Buchberger |
| 2014/0166029 A1 | 6/2014 | Weigensberg et al. |
| 2014/0311505 A1 | 10/2014 | Liu |
| 2015/0136155 A1 | 5/2015 | Verleur et al. |
| 2015/0173417 A1 | 6/2015 | Gennrich et al. |
| 2015/0173422 A1 | 6/2015 | Liu |
| 2015/0181928 A1 | 7/2015 | Liu |
| 2015/0189920 A1 | 7/2015 | Liu |
| 2016/0345631 A1 | 12/2016 | Monsees et al. |

FOREIGN PATENT DOCUMENTS

| | | |
|---|---|---|
| WO | WO-2014/195859 A2 | 12/2014 |
| WO | WO-2015179388 A1 | 11/2015 |

OTHER PUBLICATIONS

"The Next Generation Hybrid Vaping and New Way to Consume Tobacco" Jinjia Technologies, last retrieved Nov. 30, 2017, http://jinjiatech.com/PRODUCTS/Heat/91.

"British American to Test Tobacco/E-Cigarette Hybrid" Discover Thomson Reuters, Last retrieved Nov. 15, 2015, http://www.reuters.com/article/us-brit-am-tobacco-products-idUSKCN0T7U020151118.

Extended European Search Report (EESR) for European Patent Application No. 16205103 dated Jun. 16, 2017.

\* cited by examiner

AEROSOL-GENERATING SYSTEM HAVING A CARTRIDGE AND A BYPASS AIR INLET

CROSS-REFERENCE TO RELATED APPLICATIONS

This is a continuation of and claims priority to PCT/EP2017/080862, filed on Nov. 29, 2017, and further claims priority to EP 16205103.1, filed on Dec. 19, 2016, both of which are hereby incorporated by reference in their entirety.

BACKGROUND

Example embodiments relate to an aerosol-generating system (which may also be referred to as electronic vaping systems or electrically operated smoking systems) having a cartridge and an aerosol-generating device. The aerosol-generating device may have a cavity configured to receive the cartridge and a bypass air inlet.

DESCRIPTION OF RELATED ART

One type of aerosol-generating system is an electrically operated smoking system. Electrically operated smoking systems typically may comprise an aerosol-generating device comprising a battery, control electronics and an electric heater configured to heat an aerosol-forming substrate. The aerosol-forming substrate may be contained within part of the aerosol-generating device. The aerosol-generating device may comprise a liquid storage portion in which a liquid aerosol-forming substrate, such as a nicotine solution, is stored. Such devices, which may be referred to as 'e-cigarettes', may contain a liquid aerosol-forming substrate.

The e-cigarette may include a tobacco-based substrate so as to impart a tobacco taste to the aerosol inhaled by the vaper. The tobacco-based substrate may be provided in a removable cartridge.

SUMMARY

At least one example embodiment relates to an aerosol-generating system.

In at least one example embodiment, an aerosol-generating system includes a cartridge, a liquid aerosol-forming substrate, and an aerosol-generating device. The cartridge includes a cartridge housing, and a solid aerosol-forming substrate in the cartridge housing. The aerosol-generating device includes a cavity configured to receive at least a portion of the cartridge, an airflow inlet, an airflow sensor between the airflow inlet and the cavity, the airflow sensor in fluid communication with the airflow inlet and the cavity, a bypass air inlet in fluid communication with the cavity, an electric heater configured to heat the liquid aerosol-forming substrate, a power supply configured to supply power to the electric heater, and a controller configured to control a supply of electrical power from the power supply to the electric heater in response to a signal from the airflow sensor indicative of airflow across the airflow sensor. The aerosol-generating system is configured so that the cartridge housing substantially prevents airflow through the bypass air inlet when the cartridge is received within the cavity.

In at least one example embodiment, the bypass air inlet is in a sidewall of the cavity. The bypass air inlet comprises a plurality of bypass air inlets, and the aerosol-generating system is configured such that the cartridge housing substantially prevents airflow through each of the bypass air inlets when the cartridge is within the cavity.

In at least one example embodiment, the aerosol-generating device comprises a liquid storage section and the liquid aerosol-forming substrate positioned within the liquid storage section. The liquid storage section comprises a porous carrier material, and the liquid aerosol-forming substrate is on the porous carrier material.

In at least one example embodiment, the aerosol-generating device further comprises a liquid transfer element configured to transfer the liquid aerosol-forming substrate to the electric heater. The liquid aerosol-forming substrate is within the cartridge housing. The cartridge comprises a porous carrier material, and the liquid aerosol-forming substrate is on the porous carrier material. The aerosol-generating device comprises a liquid transfer element configured to transfer the liquid aerosol-forming substrate from the porous carrier material to the electric heater. The cartridge further comprises a frangible seal. The aerosol-generating device further comprises a piercing element configured to pierce the frangible seal when the cartridge is inserted into the aerosol-generating device receives. The piercing element comprises a hollow shaft portion and a piercing portion at an end of the hollow shaft portion. At least a portion of the electric heater is positioned inside the hollow shaft portion. A first portion of the liquid transfer element is inside the hollow shaft portion, and the electric heater comprises a resistive heating coil at least partially wound around the first portion of the liquid transfer element.

In at least one example embodiment, the liquid transfer element extends through an aperture in the hollow shaft portion, and a second portion of the liquid transfer element overlies an outer surface of the hollow shaft portion.

In at least one example embodiment, the porous carrier material has an annular shape. The porous carrier material defines a passage therein. The aerosol-generating system is configured such that the piercing element is at least partially received within the passage when the aerosol-generating device receives the cartridge. The aerosol-generating system is configured such that the second portion of the liquid transfer element contacts an inner surface of the porous carrier material when the piercing portion is at least partially received within the passage.

In at least one example embodiment, the cartridge further comprises an airflow channel between the porous carrier material and the cartridge housing, and a downstream end of the airflow channel is in fluid communication with the solid aerosol-forming substrate.

BRIEF DESCRIPTION OF THE DRAWINGS

At least one example embodiment is further described, by way of example only, with reference to the accompanying drawings.

DETAILED DESCRIPTION

Figure 1:
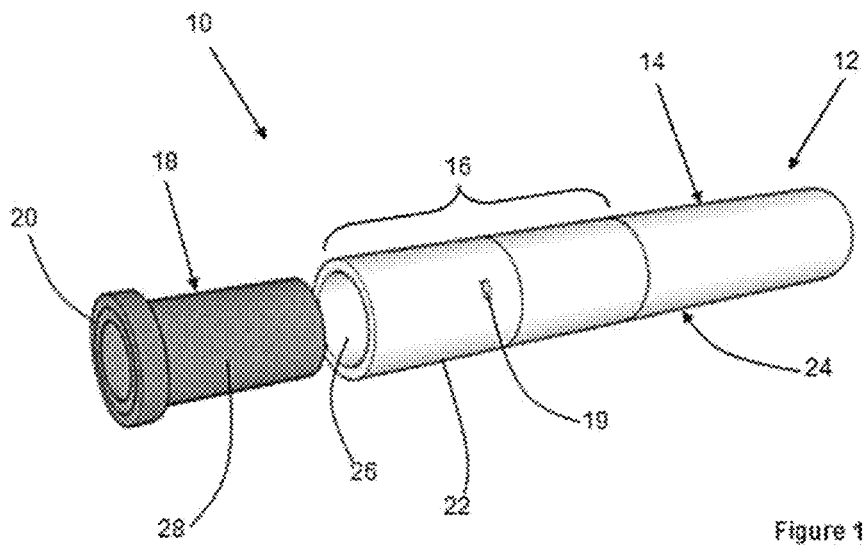
FIG. 1 is a perspective view of an aerosol-generating system according to at least one example embodiment.
Figure 2:
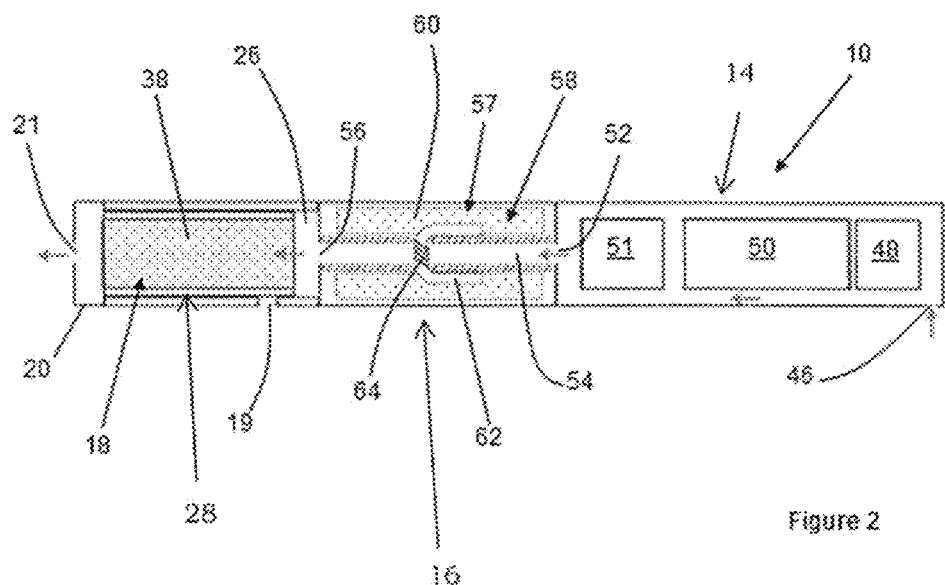
FIG. 2 is a cross-sectional view of the aerosol-generating system of FIG. 1 with the cartridge received in the cavity according to at least one example embodiment.
Figure 3:
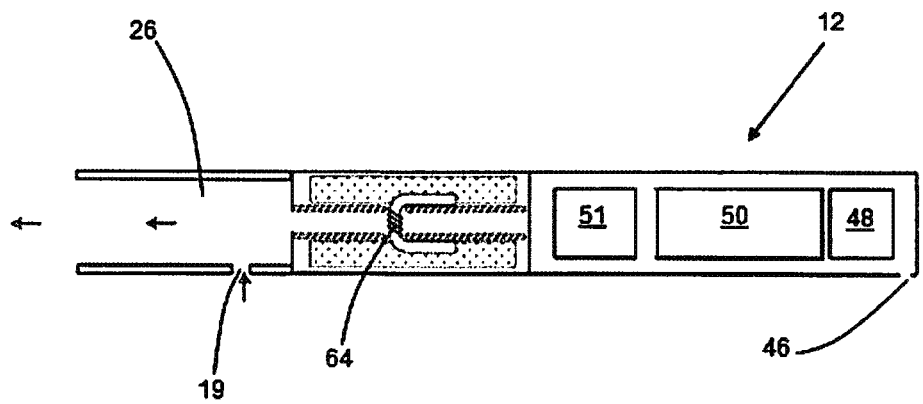
FIG. 3 is an illustration of the aerosol-generating device of FIG. 2 without the cartridge inserted into the cavity according to at least one example embodiment.
Figure 4:
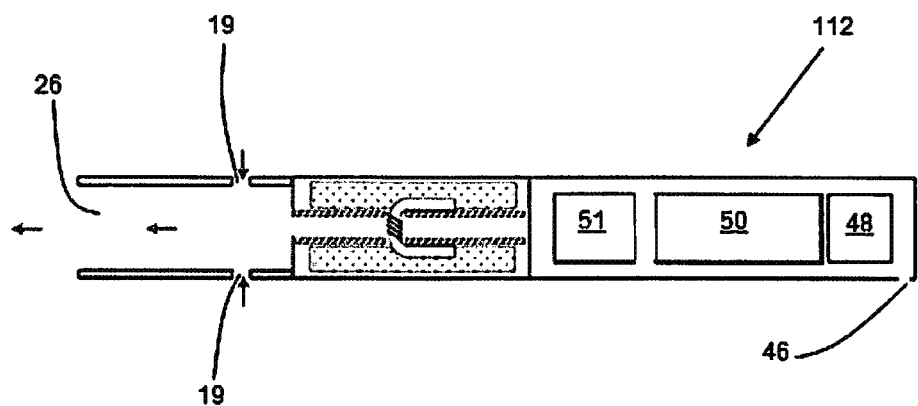
FIG. 4 is a cross-sectional view of an aerosol-generating device according to at least one example embodiment.
Figure 5:
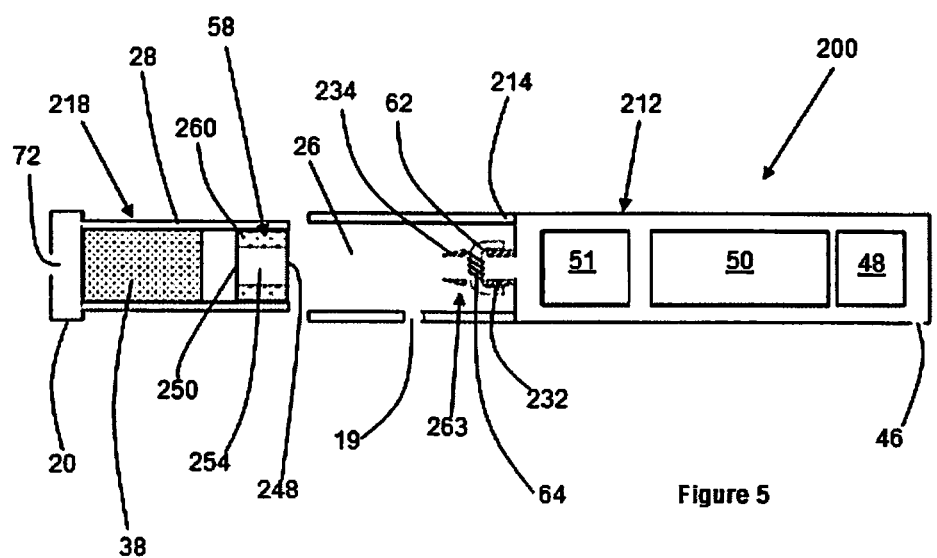
FIG. 5 is a cross-sectional view of an aerosol-generating system with the cartridge separate from the aerosol-generating device according to at least one example embodiment.
Figure 6:
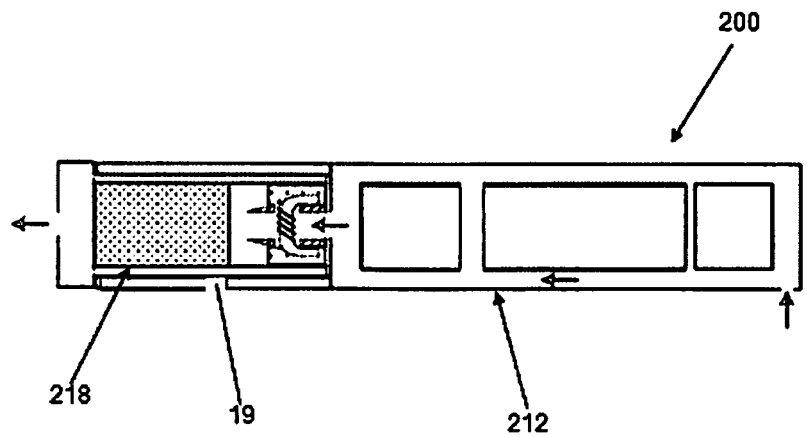
FIG. 6 is a cross-sectional view of the aerosol-generating system of FIG. 5 with the cartridge received within the cavity according to at least one example embodiment.
Figure 7:
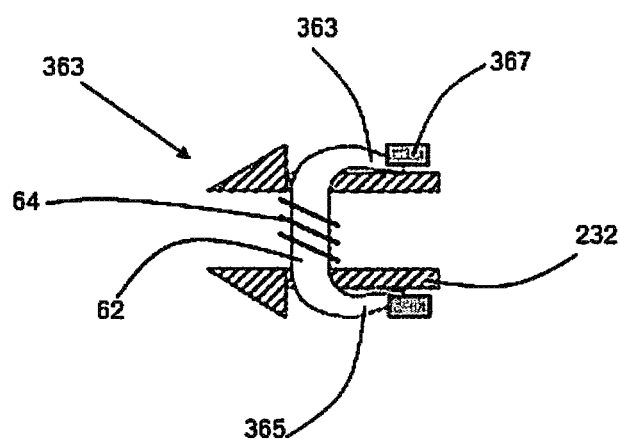
FIG. 7 is an illustration of a heater section of the aerosol-generating system of FIG. 5 according to at least one example embodiment.

It should be understood that when an element or layer is referred to as being "on," "connected to," "coupled to," or "covering" other element or layer, it may be directly on, connected to, coupled to, or covering the other element or layer or intervening elements or layers may be present. In contrast, when an element is referred to as being "directly on," "directly connected to," or "directly coupled to" another element or layer, there are no intervening elements or layers present. Like numbers refer to like elements throughout the specification. As used herein, the term "and/or" includes any and all combinations of one or more of the associated listed items.

It should be understood that, although the teems first, second, third, etc. may be used herein to describe various elements, components, regions, layers and/or sections, these elements, components, regions, layers, and/or sections should not be limited by these terms. These terms are only used to distinguish one element, component, region, layer, or section from another region, layer, or section. Thus, a first element, component, region, layer, or section discussed below could be termed a second element, component, region, layer, or section without departing from the teachings of example embodiments.

Spatially relative terms (e.g. "beneath," "below," "lower," "above," "upper," and the like) may be used herein for ease of description to describe one element or feature's relationship to another element(s) or feature(s) as illustrated in the figures. It should be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" may encompass both an orientation of above and below. The device may be otherwise oriented (rotated 90 degrees or at other orientations) and the spatially relative descriptors used herein interpreted accordingly.

The terminology used herein is for the purpose of describing various embodiments only and is not intended to be limiting of example embodiments. As used herein, the singular forms "a," an, and "the" are intended to include the plural forms as well, unless the context clearly indicates otherwise. It will be further understood that the terms "includes," "including," "comprises," and/or "comprising," when used in this specification, specify the presence of stated features, integers, steps, operations, elements, and/or components, but do riot preclude the presence or addition of one or more other features, integers, steps, operations, elements, components, and/or groups thereof.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the shapes of regions illustrated herein but are to include deviations in shapes that result, for example, from manufacturing.

Unless otherwise defined, all terms (including technical and scientific terms) used herein have the same meaning as commonly understood. by one of ordinary skill in the art to which example embodiments belong. It will be further understood that terms, including those defined in commonly used dictionaries, should be interpreted as having a meaning that is consistent with their meaning in the context of the relevant art and will not be interpreted in an idealized or overly formal sense unless expressly so defined herein.

According to at least one example embodiment, an aerosol-generating system includes a cartridge, a liquid aerosol-forming substrate, and an aerosol-generating device. The cartridge includes a cartridge housing and a solid aerosol-forming substrate within the cartridge housing. The aerosol-generating device comprises a cavity configured to receive at least a portion of the cartridge, an airflow inlet, and an airflow sensor between the airflow inlet and the cavity. The airflow sensor is in fluid communication with the airflow inlet and the cavity. The aerosol-generating device may further comprise a bypass air inlet in fluid communication with the cavity, an electric heater configured to heat the liquid aerosol-forming substrate, a power supply, and a controller. The controller is configured to control a supply of electrical power from the power supply to the electric heater in response to a signal from the airflow sensor indicative of airflow across the airflow sensor. The aerosol-generating system is configured such that the cartridge housing substantially prevents airflow through the bypass air inlet when the cartridge is received within the cavity.

The liquid aerosol-forming substrate may form part of the cartridge or part of the aerosol-generating device.

As used herein, the term "aerosol-forming substrate" is used to describe a substrate configured to release volatile compounds, which can form an aerosol. The aerosols generated from aerosol-forming substrates of aerosol-generating systems may be visible or invisible and may include vapours (for example, fine particles of substances, which are in a gaseous stale, that are ordinarily liquid or solid at room temperature) as well as gases and liquid droplets of condensed vapours.

When a vaper draws on the aerosol-generating device without the cartridge inserted into the cavity, air is drawn into the aerosol-generating device via the bypass air inlet. In this example embodiment, there is insufficient airflow across the airflow sensor to trigger the airflow sensor. Thus, when a vaper draws on the aerosol-generating device without the cartridge inserted into the cavity, the controller does not activate the electric heater.

When the cartridge is received within the cavity, the bypass air inlet is blocked by the cartridge housing. Thus, when a vaper draws on the aerosol-generating device with the cartridge inserted into the cavity, air can only flow into the aerosol-generating device via the airflow inlet. In this example embodiment, there is sufficient airflow across the airflow sensor to trigger the airflow sensor. Thus, when a vaper draws on the aerosol-generating device with the cartridge inserted into the cavity, the controller activates the electric heater.

The aerosol-generating system may comprise an airflow outlet. When the cartridge is received within the cavity, the aerosol-generating system comprises an airflow path extending through the aerosol-generating system from the airflow inlet to the airflow outlet.

The bypass air inlet may be positioned on a sidewall of the cavity. A sidewall of the cavity is a wall along which the cartridge housing slides when the cartridge is inserted into the cavity. Providing the bypass air inlet on a sidewall of the cavity may facilitate obstruction of the bypass air inlet by the cartridge housing when the cartridge is received within the cavity.

The bypass air inlet may comprise a plurality of bypass air inlets. The aerosol-generating system s configured such that the cartridge housing substantially prevents airflow through each of the bypass air inlets when the cartridge is received within the cavity. Providing a plurality of bypass air inlets may increase the ratio of airflow through the bypass air inlets to airflow through the airflow inlet when the cartridge is not received within the cavity. Therefore, this arrangement may further reduce the airflow across the airflow sensor when a vaper draws on the aerosol-generating system without the cartridge received within the cavity.

The aerosol-generating device may comprise a liquid storage section. The liquid aerosol-forming substrate is positioned within the liquid storage section. The aerosol-generating device comprises a power supply section comprising the power supply and the controller. The liquid storage section is configured to be removably attached to the power supply section.

The liquid storage section may comprise a porous carrier material. The liquid aerosol-forming substrate may be on the porous carrier material. Providing the liquid aerosol-forming substrate on a porous carrier material may reduce the risk of the liquid aerosol-forming substrate leaking from the liquid storage section.

The aerosol-generating system may further comprise a liquid transfer element configured so that, during vaping, liquid aerosol-forming substrate is transported by capillary action along the liquid transfer element from the liquid storage section to the electric heater. In at least one example embodiment in which the liquid storage section comprises a porous carrier material, the liquid transfer element may be configured to transport the liquid aerosol-forming substrate from the porous carrier material to the electric heater.

The electric heater may be provided separately from one or both of the liquid storage section and the power supply section. In at least one example embodiment, the liquid storage section, the electric heater and, where present, the liquid transfer element are provided together in a vaporiser section. In at least one example embodiment, the vaporiser section comprises a vaporiser housing forming part of a device housing. The vaporiser housing comprises an upstream end configured to be connected to the power supply section and a downstream end defining a cavity configured to receive the cartridge assembly. Providing the liquid storage section, the electric heater and, where present, the liquid transfer element in a single vaporiser section separate from the power supply section may facilitate replacement of the vaporiser section (for example, when the liquid aerosol-forming substrate has been depleted) without the need to replace the power supply section.

The cartridge may comprise the liquid aerosol-forming substrate positioned within the cartridge housing.

The cartridge may comprise a porous carrier material, wherein the liquid aerosol-forming substrate is provided on the porous carrier material. In at least one example embodiment, providing the liquid aerosol-forming substrate on a porous carrier material may reduce the risk of the liquid aerosol-forming substrate leaking from the cartridge.

The aerosol-generating device may comprise a liquid transfer element configured to transfer liquid aerosol-forming substrate from the cartridge to the electric heater when the cartridge is received within the cavity. In at least one example embodiment in which the cartridge comprises a porous carrier material, the liquid transfer element is configured to transport liquid aerosol-forming substrate from the porous carrier material to the electric heater.

The cartridge may comprise a seal. The seal may be a removable seal or a frangible seal. In at least one example embodiment, the seal may substantially prevent the loss of volatile compounds from one or both of the solid aerosol-forming substrate and the liquid aerosol-forming substrate. The cartridge may comprise a seal extending across a first end of the cartridge housing. In at least one example embodiment, the first end is the upstream end of the cartridge housing. The seal may be secured to the cartridge housing about a periphery of the seal. The seal may be secured to the cartridge housing by at least one of an adhesive and a weld, such as an ultrasonic weld. The seal may be formed from a sheet material. The sheet material may comprise at least one of a polymeric film and a metallic foil. In at least one example embodiment in which the seal is a removable seal, the removable seal may be configured to be removed from the cartridge by a vapor before combining e cartridge with the aerosol-generating device. The removable seal may comprise a pull tab to facilitate removal of the seal.

In at least one example embodiment in which the seal is a frangible seal, the aerosol-generating device comprises a piercing element configured to pierce the frangible seal when the aerosol-generating device receives the cartridge. In at least one example embodiment, the piercing element may automatically pierce the frangible seal when the aerosol-generating device and the heater section are combined with the cartridge.

At least a portion of the electric heater may form the piercing element. The electric heater may be in the form of a heater blade configured to pierce the frangible seal.

The piercing element may be formed separately from the electric heater. The piercing element may comprise a hollow shaft portion and a piercing portion at an end of the hollow shaft portion. In at least one example embodiment, a hollow shaft portion may allow airflow through the hollow shaft portion during vaping of the aerosol-generating system. The piercing portion may comprise an airflow aperture extending through the piercing portion and in fluid communication with the interior of the hollow shaft portion. At least a portion of the interior of the hollow shaft portion may define an airflow passage extending along at least a portion of the hollow shaft portion. The airflow passage is in fluid communication with the airflow inlet, the airflow sensor and the cavity. The airflow sensor may be positioned upstream of the airflow passage. The airflow sensor may be positioned downstream of the airflow passage.

At least a portion of the electric heater may be positioned inside the hollow shaft portion. At least a portion of the electric heater may extend transversely across a portion of the airflow passage. In at least one example embodiment, the electric heater and the hollow shaft portion are configured so that, during vaping, airflow through the airflow passage passes across the portion of the electric heater positioned inside the hollow shaft portion.

In at least one example embodiment in which the aerosol-generating device comprises a liquid transfer element, a first portion of the liquid transfer element may be positioned inside the hollow shaft portion. The first portion of the liquid transfer element may extend transversely across a portion of the airflow passage. In at least one example embodiment, the liquid transfer element and the hollow shaft portion are configured so that, during vaping, airflow through the airflow passage passes across the first portion of the liquid transfer element.

The electric heater may comprise a resistive heating coil. In at least one example embodiment, the resistive heating coil is at least partially wound around the first portion of the liquid transfer element.

The liquid transfer element may extend through a first aperture in the hollow shaft portion. A second portion of the liquid transfer element overlies an outer surface of the hollow shaft portion. The second portion of the liquid transfer element is a first end of the liquid transfer element. The liquid transfer element may extend through a second aperture in the hollow shaft portion, wherein a third portion of the liquid transfer element overlies the outer surface of the hollow shaft portion. The second aperture is opposite the first aperture. The third portion of the liquid transfer element is a second end of the liquid transfer element. The first portion of the liquid transfer element is an intermediate portion of the liquid transfer element between the second and third portions.

The aerosol-generating device may comprise a securing ring positioned around part of the hollow shaft portion. At least part of the second portion of the liquid transfer element is between the securing ring and the hollow shaft portion. In at least one example embodiment in which the liquid transfer element comprises a third portion overlying the outer surface of the hollow shaft portion, at least part of the third portion of the liquid transfer element is positioned between the securing ring and the hollow shaft portion.

In at least one example embodiment in which the cartridge comprises a porous carrier material, the porous carrier material may have an annular shape defining a passage through the porous carrier material. When the cartridge is received within the cavity, the passage defined through the porous carrier material may form part of an airflow path through the aerosol-generating system.

In at least one example embodiment, the aerosol-generating system is configured such that the piercing element is at least partially received within the passage when the aerosol-generating device receives the cartridge. In at least one example embodiment, the aerosol-generating system is configured such that the second portion of the liquid transfer element contacts an inner surface of the porous carrier material when the piercing portion is at least partially received within the passage. In at least one example embodiment in which the liquid transfer element comprises a third portion, the aerosol-generating system is configured such that the third portion of the liquid transfer element contacts the inner surface of the porous carrier material when the piercing portion is at least partially received within the passage.

In at least one example embodiment, the piercing portion is tapered and may have a maximum diameter at a first end of the piercing portion adjacent the hollow shaft portion. In at least one example embodiment, the piecing portion comprises a minimum diameter at a second end of the piercing portion. The second end of the piercing portion is configured to pierce the frangible seal of the cartridge.

In at least one example embodiment, the hollow shaft portion has a first diameter adjacent the first end of the piercing portion. The first diameter of the hollow shaft portion is less than the maximum diameter of the piercing portion. In at least one example embodiment in which the aerosol-generating device comprises a liquid transfer element having a second portion overlying an outer surface of the hollow shaft portion, the maximum thickness of the second portion of the liquid transfer element is equal to or less than the difference between the maximum diameter and the first diameter. In at least one example embodiment in which the liquid transfer element has a third portion overlying the outer surface of the hollow shaft portion, the maximum combined thickness of the second and third portions of the liquid transfer element is equal to or less than the difference between the maximum diameter and the first diameter. Such arrangements may reduce stress on the liquid transfer element when the cartridge is combined with the aerosol-generating device, particularly in example embodiments in which the piercing element is received within a passage extending through the porous carrier material.

In at least one example embodiment in which the cartridge comprises a porous carrier material, the cartridge may comprise an airflow channel between the porous carrier material and the cartridge housing. In at least one example embodiment, a downstream end of the airflow channel is in fluid communication with the solid aerosol-forming substrate. The airflow channel may be in addition to, or alternative to, a passage extending through the porous carrier material.

In at least one example embodiment, the cartridge housing is tubular and comprises a first, upstream end and a second, downstream end. In at least one example embodiment, the solid aerosol-forming substrate is positioned within the downstream end. In at least one example embodiment, the liquid aerosol-forming substrate is positioned within the upstream end.

In at least one example embodiment in which the cartridge comprises a porous carrier material on which the liquid aerosol-forming substrate is positioned, the porous carrier material may be positioned directly within the cartridge housing. In at least one example embodiment, the porous carrier material is retained within the cartridge housing by an interference fit.

The porous carrier material may be positioned within a liquid storage housing, wherein the liquid storage housing is positioned within the cartridge housing. In at least one example embodiment, the liquid storage housing is retained within the cartridge housing by an interference fit.

In at least one example embodiment in which the cartridge comprises an airflow channel positioned between the porous carrier material and the cartridge housing, an outer surface of the liquid storage housing may be shaped to define the airflow channel between the cartridge housing and the liquid storage housing when the liquid storage housing is received within the cartridge housing. The outer surface of the liquid storage housing may comprise a groove to define the airflow channel when the liquid storage housing is received within the cartridge housing.

The liquid storage housing may be tubular. In at least one example embodiment in which the cartridge comprises a removable seal or a frangible seal, the seal may extend across the upstream end of the liquid storage housing. In at least one example embodiment, the seal is secured to the liquid storage housing instead of the cartridge housing.

The tubular liquid storage housing may have an open upstream end and a closed downstream end. In at least one example embodiment in which the cartridge comprises a removable seal or a frangible seal, the seal may extend across the upstream end of the liquid storage housing such that the porous carrier material is between the seal and the closed end.

The solid aerosol-forming substrate may be retained in the cartridge housing by an interference fit.

The cartridge may comprise a filter positioned downstream of the solid aerosol-forming substrate. The filter may comprise a plug of filter material positioned within the downstream end of the cartridge housing. The plug of filter material may be retained within the cartridge housing by an interference fit. The filter may comprise a sheet material extending across a downstream opening of the cartridge housing. The sheet material may comprise a mesh. The sheet material may be secured to the cartridge housing by at least one of an adhesive and a weld, such as an ultrasonic weld. The filter may retain the solid aerosol-forming substrate in the cartridge housing.

The aerosol-generating system may comprise a mouthpiece. In at least one example embodiment in which the aerosol-generating system comprises at least one airflow outlet, the mouthpiece comprises the at least one airflow outlet. The mouthpiece may form part of the cartridge. The mouthpiece may form part of the aerosol-generating device. The mouthpiece may be formed separately from the cartridge and the aerosol-generating device. At least one of the cartridge and the aerosol-generating device is configured to receive the mouthpiece.

The solid aerosol-forming substrate may comprise tobacco. The solid aerosol-forming substrate may comprise a tobacco-containing material containing volatile tobacco flavour compounds which are released from the substrate upon heating.

The solid aerosol-forming substrate may comprise tobacco containing deprotonated nicotine. Deprotonating the nicotine within tobacco may increase the volatility of the nicotine. Nicotine may be deprotonated by subjecting the tobacco to an alkalising treatment.

The solid aerosol-forming substrate may comprise a non-tobacco material. The solid aerosol-forming substrate may comprise tobacco-containing material and non-tobacco containing material.

The solid aerosol-forming substrate may include at least one aerosol-former. As used herein, the term 'aerosol former' is used to describe any suitable known compound or mixture of compounds that, in use, facilitates formation of an aerosol. Suitable aerosol-formers include, but are not limited to polyhydric alcohols, such as propylene glycol, triethylene glycol, 1,3-butanediol and glycerine; esters of polyhydric alcohols, such as glycerol mono-, di- or triacetate; and aliphatic esters of mono-, di- or polycarboxylic acids, such as dimethyl dodecanedioate and dimethyl tetradecanedioate In at least one example embodiment, the aerosol formers are polyhydric alcohols or mixtures thereof, such as propylene glycol, triethylene glycol 1,3-butanediol and, glycerine.

The solid aerosol-forming substrate may comprise a single aerosol former. Alternatively, the solid aerosol-forming substrate may comprise a combination of two or more aerosol formers.

The solid aerosol-forming substrate may have an aerosol former content of greater than 5 percent on a dry weight basis.

The solid aerosol-forming substrate may have an aerosol former content of ranging from about 5 percent to about 30 percent on a dry weight basis.

The solid aerosol-forming substrate may have an aerosol former content of about 20 percent on a dry weight basis.

The liquid aerosol-forming substrate may comprise a tobacco-containing material comprising volatile tobacco flavour compounds which are released from the liquid upon heating. The liquid aerosol-forming substrate may comprise a non-tobacco material. The liquid aerosol-forming substrate may include water, solvents, ethanol, plant extracts and natural or artificial flavours. In at least one example embodiment, the liquid aerosol-forming substrate comprises an aerosol former. Suitable aerosol formers include polyhydric alcohols or mixtures thereof, such as propylene glycol, triethylene glycol, 1,3-butanediol and glycerine.

The liquid aerosol-forming substrate may comprise nicotine.

The liquid aerosol-forming substrate may be free from nicotine. In at least one example embodiment, the vaporised liquid aerosol-forming substrate may be drawn through the solid aerosol-forming substrate during use to strip one or more volatile compounds from the solid aerosol-forming substrate. The vaporised liquid aerosol-forming substrate may strip nicotine from the solid-aerosol-forming substrate. A solid aerosol-forming substrate comprising tobacco containing deprotonated nicotine may be particularly suited to embodiments in which the liquid aerosol-forming substrate is free from nicotine.

The electric heater may comprise a resistive heating coil. The aerosol-generating device may comprise a heater support. The resistive heating coil is at least partially wound around the heater support.

The electric heater may comprise a resistive heating mesh.

The resistive heating mesh may comprise a plurality of electrically conductive filaments. The electrically conductive filaments may be substantially flat. As used herein, "substantially flat" means formed in a single plane and not wrapped around or otherwise conformed to fit a curved or other non-planar shape. A flat heating mesh can be easily handled during manufacture and provides for a robust construction.

The electrically conductive filaments may define interstices between the filaments and the interstices may have a width of ranging from about 10 micrometres to about 100 micrometres. In at least one example embodiment, the filaments give rise to capillary action in the interstices, so that during vaping, liquid aerosol-forming substrate is drawn into the interstices, increasing the contact area between the heater assembly and the liquid.

The electrically conductive filaments may form a mesh of size ranging from about 160 Mesh US to about 600 Mesh US (+1-10%) (that is, from about 160 to about 600 filaments per inch (+/−10%)). The width of the interstices ranges from about 75 micrometres to about 25 micrometres. The percentage of open area of the mesh, which is the ratio of the area of the interstices to the total area of the mesh may range from about 25 percent to about 56 percent. The mesh may be formed using different types of weave or lattice structures. The electrically conductive filaments may be an array of filaments arranged parallel to one another.

The electrically conductive filaments may have a diameter ranging from about 8 micrometres to about 100 micrometres, from about 8 micrometres to about 50 micrometres, or from about 8 micrometres to about 39 micrometres.

The resistive heating mesh may cover an area of less than or equal to about 25 square millimetres. The resistive heating mesh may be rectangular. The resistive heating mesh may be square. In at least one example embodiment, the resistive heating mesh may have dimensions of about 5 millimetres by about 2 millimetres.

The electrically conductive filaments may comprise any suitable electrically conductive material. Suitable materials include but are not limited to: semiconductors such as doped ceramics, electrically "conductive" ceramics (such as, for example, molybdenum disilicide), carbon, graphite, metals, metal alloys and composite materials made of a ceramic material and a metallic material. Such composite materials may comprise doped or undoped ceramics. Examples of suitable doped ceramics include doped silicon carbides. Examples of suitable metals include titanium, zirconium, tantalum and metals from the platinum group. Examples of suitable metal alloys include stainless steel, constantan, nickel-, cobalt-, chromium-, aluminium- titanium- zirconium-, hafnium-, niobium-, molybdenum-, tantalum-, tungsten-, tin-, gallium-, manganese- and iron-containing alloys, and super-alloys based on nickel, iron, cobalt, stainless steel, Timetal®, iron-aluminium based alloys and iron-manganese-aluminium based alloys. Timetal® is a registered trade mark of Titanium Metals Corporation. The filaments may be coated with one or more insulators. Materials for the electrically conductive filaments include 304, 316, 304L, and 316L stainless steel, and graphite.

The electrical resistance of the resistive heating mesh may range from about about 0.3 Ohms to about 4 Ohms. In at least one example embodiment, the electrical resistance of the mesh ranges from about 0.5 to about 3 Ohms. In at least one example embodiment, the electrical resistance of the mesh is about 1 Ohm.

In at least one example embodiment in which the electric heater comprises a resistive heating coil, the pitch of the coil ranges from about 0.5 millimetres to about 1.5 millimetres. In at least one example embodiment in which the electric heater comprises a resistive heating coil, the pitch of the coil is about 1.5 millimetres. The pitch of the coil means the spacing between adjacent turns of the coil. The coil may comprise fewer than six turns, and may have fewer than five turns. The coil may be formed from an electrically resistive wire having diameter ranging from about 0.10 millimetres to about 0.15 millimetres, or about 0.125 millimetres. The electrically resistive wire is formed of 904 or 301 stainless steel. Examples of other suitable metals include titanium, zirconium, tantalum and metals from the platinum group. Examples of other suitable metal alloys include, Constantan, nickel-, cobalt-, chromium-, aluminium- titanium- zirconium-, hafnium-, niobium-, molybdenum-, tantalum-, tungsten-, tin-, gallium-, manganese- and iron-containing alloys, and super-alloys based on nickel, iron, cobalt, stainless steel, Timetal®, iron-aluminium based alloys and iron-manganese-aluminium based alloys. The resistive heating coil may also comprise a metal foil, such as an aluminium foil, which is provided in the form of a ribbon.

In at least one example embodiment in which the aerosol-generating system comprises a porous carrier material, the porous carrier material may comprise any suitable material or combination of materials which is permeable to the liquid aerosol-forming substrate and allows the liquid aerosol-forming substrate to migrate through the porous carrier material. In at least one example embodiment, the material or combination of materials is inert with respect to the liquid aerosol-forming substrate. The porous carrier material may or may not be a capillary material. The porous carrier material may comprise a hydrophilic material to improve distribution and spread of the liquid aerosol-forming substrate. This may assist with consistent aerosol formation. The particular material or materials will depend on the physical properties of the liquid aerosol-forming substrate. Examples of suitable materials are a capillary material, for example a sponge or foam material, ceramic- or graphite-based materials in the form of fibres or sintered powders, a foamed metal or plastics material, a fibrous material, for example made of spun or extruded fibres, such as cellulose acetate, polyester, or bonded. polyolefin, polyethylene, terylene or polypropylene fibres, nylon fibres or ceramic. The porous carrier material may have any suitable porosity so as to be used with different liquid physical properties.

In at least one example embodiment in which the aerosol-generating system comprises a liquid transfer element, the liquid transfer element may comprise any suitable material or combination of materials which is able to convey the liquid aerosol-forming substrate along its length. The liquid transfer element may be formed from a porous material, but this need not be the case. The liquid transfer element may be formed from a material having a fibrous or spongy structure. The liquid transfer element comprises a bundle of capillaries. In at least one example embodiment, the liquid transfer element may comprise a plurality of fibres or threads or other fine bore tubes. The liquid transfer element may comprise sponge-like or foam-like material. In at least one example embodiment, the structure of the liquid transfer element forms a plurality of small bores or tubes, through which the liquid aerosol-forming substrate can be transported by capillary action. The material or materials will depend on the physical properties of the liquid aerosol-forming substrate. Examples of suitable capillary materials include a sponge or foam material, ceramic- or graphite-based materials in the form of fibres or sintered powders, foamed metal or plastics material, a fibrous material, for example made of spun or extruded fibres, such as cellulose acetate, polyester, or bonded polyolefin, polyethylene, terylene or polypropylene fibres, nylon fibres, ceramic, glass fibres, silica glass fibres, carbon fibres, metallic fibres of medical grade stainless steel alloys such as austenitic 316 stainless steel and martensitic 440 and 420 stainless steels. The liquid transfer element may have any suitable capillarity so as to be used with different liquid physical properties. The liquid aerosol-forming substrate has physical properties, including but not limited to viscosity, surface tension, density, thermal conductivity, boiling point and vapour pressure, which allow the liquid aerosol-forming substrate to be transported through the liquid transfer element. The liquid transfer element may be formed from heat-resistant material. The liquid transfer element may comprise a plurality of fibre strands. The plurality of fibre strands may be generally aligned along a length of the liquid transfer element.

In at least one example embodiment in which the aerosol-generating system comprises a porous carrier material and a liquid transfer element, the porous carrier material and the liquid transfer element may comprise the same material. In at least one example embodiment, the porous carrier material and the liquid transfer element comprise different materials.

In at least one example embodiment, the cartridge is configured to be retained within the cavity by an interference fit. Each of the cartridge and the cavity may have any suitable cross-sectional shape. In at least one example embodiment, a cross-sectional shape of the cartridge is substantially the same as a cross-sectional shape of the cavity. Suitable cross-sectional shaped include circular, semi-circular, polygonal, such as rectangular, including square, and irregular shapes.

The cartridge housing may be formed from any suitable material or combination of materials. Suitable materials include, but are not limited to, aluminium, polyether ether ketone (PEEK), polyimides, such as Kapton®, polyethylene terephthalate (PET), polyethylene (PE), high-density polyethylene (HDPE), polypropylene (PP), polystyrene (PS), fluorinated ethylene propylene (FEP), polytetrafluoroethylene (PTFE), polyoxymethylene (POM), epoxy resins, polyurethane resins, vinyl resins, liquid crystal polymers (LCP) and modified. LCPs, such as LCPs with graphite or glass fibres.

The power supply may comprise a battery. For example, the power supply may be a nickel-metal hydride battery, a nickel cad m battery, or a lithium based battery, for example a lithium-cobalt, a lithium-iron-phosphate or a lithium-polymer battery. The power supply may alternatively be another form of charge storage device such as a capacitor. The power supply may require recharging and may have a capacity that allows for the storage of enough energy for use of the aerosol-generating device with more than one cartridge.

FIG. 1 is an illustration of a perspective view of an aerosol-generating system 10 according to at least one example embodiment. The aerosol-generating system 10 comprises an aerosol-generating device 12 comprising a power supply section 14 and a vaporiser section 16. The aerosol-generating system 10 further comprises a cartridge 18 and a mouthpiece 20 forming part of the cartridge 18. The vaporiser section 16 comprises a vaporiser housing 22 that forms part of a device housing 24. A downstream end of the vaporiser housing 22 defines a cavity 26 configured to receive at least a portion of the cartridge 18. The vaporiser housing 22 also defines a bypass air inlet 19 in fluid communication with the cavity 26.

FIG. 2 is a cross-sectional view of the aerosol-generating system 10 with the cartridge 18 received within the cavity 26. The cartridge 18 comprises a cartridge housing 28 and a solid aerosol-forming substrate 38 positioned within the cartridge housing 28. A downstream end of the solid aerosol-forming substrate 38 is in fluid communication with an airflow outlet 21 defined by the mouthpiece 20.

The power supply section 14 comprises a system air inlet 46 for admitting air into the power supply section 14. Positioned within the power supply section 14 are a controller 48, a power supply 50 and an airflow sensor 51. The airflow sensor 51 is configured to provide a signal to the controller 48 when airflow across the airflow sensor 51 exceeds a predetermined threshold.

The vaporiser section 16 comprises a vaporiser air inlet 52 for receiving air from the power supply section 14, an airflow passage 54 in fluid communication with the vaporiser air inlet 52 at its upstream end, and a cavity air inlet 56 providing fluid communication between the downstream end of the airflow passage 54 and the cavity 26.

The vaporiser section 16 further comprises a liquid storage section 57 comprising a liquid aerosol-forming substrate 58 absorbed into an annular porous carrier material 60 positioned outside of the airflow passage 54. A liquid transfer element 62 comprising a capillary wick has first and second ends positioned in contact with the porous carrier material 60 and a central portion positioned within the airflow passage 54. The liquid aerosol-forming substrate 58 is wicked by capillary action along the capillary wick from the porous carrier material 60 to the central portion of the capillary wick.

The vaporiser section 16 also comprises an electric heater 64 comprising a resistive heating coil wound around the central portion of the capillary wick. During operation of the aerosol-generating system 10, the controller 48 controls a supply of electrical energy from the power supply 50 to the electric heater 64 to heat and vaporise the liquid aerosol-forming substrate 58 from the central portion of the capillary wick.

When the cartridge 18 is received within the cavity 26, as shown in FIG. 2, the cartridge housing 28 obstructs the bypass air inlet 19 to substantially prevent airflow into the cavity 26 via the bypass air inlet 19. In this configuration, when a vaper draws on the mouthpiece 20, air is drawn into the system through the system air inlet 46. As airflow enters the power supply section 14 through the airflow inlet 46, airflow across the airflow sensor 51 activates the airflow sensor 51. The activated airflow sensor 51 provides a signal to the controller 48 to indicate airflow through the aerosol-generating system 10 via the airflow inlet 46. Upon receipt of the signal from the airflow sensor 51, the controller 48 controls a supply of electrical energy from the power supply 50 to the electric heater 64 to vaporise liquid aerosol-forming substrate 58 from the liquid transfer element 62. Airflow from the power supply section 14 flows through the vaporiser air inlet 52 and into the airflow passage 54 where the vaporised liquid aerosol-forming substrate 58 is entrained in the airflow. The airflow then flows through the cavity air inlet 56, into the cavity 26 and the cartridge 18 where volatile compounds from the cartridge aerosol-forming substrate 38 are entrained in the airflow. The airflow then flows out of the cartridge 18 and out of the aerosol-generating system 10 through the air outlet 21.

When the cartridge 18 is not received within the cavity 26, as shown in FIG. 3, the bypass air inlet 19 is unobstructed. Therefore, in this configuration, when a vaper attempts to draw on a downstream end of the aerosol-generating device, airflow enters the cavity 26 via the bypass air inlet 19. As such, insufficient airflow is drawn into the power supply section 14 via the airflow inlet 46 and the airflow sensor 51 is not activated. Therefore, when the cartridge 18 is not received in the cavity 26, a vaper may not activate the electric heater 64 by drawing on the downstream end of the aerosol-generating device 12.

FIG. 4 is an illustration of an aerosol-generating device 112 according to at least one example embodiment. The aerosol-generating device 112 is substantially the same as the aerosol-generating device 12 shown in. FIGS. 1 to 3 and like reference numerals are used to designate like parts. The aerosol-generating device 112 differs by the addition of a second bypass air inlet 19. Providing an additional bypass air inlet 19 may increase the ratio of airflow through the bypass air inlets 19 to airflow through the airflow inlet 46 when the cartridge 18 is not received within the cavity 26. Therefore, this arrangement may further reduce the airflow across the airflow sensor 51 when a vaper draws on the aerosol-generating device 112 without the cartridge 18 received within the cavity 26.

FIG. 5 is an illustration of an aerosol-generating system 200 according to at least one example embodiment. The aerosol-generating system 200 is substantially the same as the aerosol-generating system 10 shown in FIGS. 1 to 3 and like reference numerals are used to designate like parts.

The aerosol-generating system 200 differs by the location of the liquid aerosol-forming substrate 58, which is positioned within the cartridge 218 instead of in the vaporiser section 16 of FIG. 2.

The cartridge 218 comprises a cartridge housing 28, and a solid aerosol-forming substrate 38 and a liquid aerosol-forming substrate 58 positioned within the cartridge housing 36. The solid aerosol-forming substrate 38 comprises a tobacco plug positioned within the downstream end of the cartridge housing 28.

The liquid aerosol-forming substrate 58 is provided on a porous carrier material 260 positioned within the upstream end of the cartridge housing 28. A first frangible seal 248 extends across the upstream end of the porous carrier material 260 and a second frangible seal 250 extends across the downstream end of the porous carrier material 260. The porous carrier material 260 has an annular shape and defines a passage 254 through the porous carrier material 260, the passage 254 extending between the first and second frangible seals 248, 250.

The aerosol-generating device 212 comprises a power supply section housing a controller 48, a power supply 50 and an airflow sensor 51, as described with respect to the aerosol-generating system 10 of FIGS. 1 to 3. The device housing 214 defines a cavity 26 configured to receive the cartridge 218.

The aerosol-generating device 212 further comprises a heater section 263 at an upstream end of the cavity 26. The heater section 263 comprises an electric heater 64 in the form of a resistive heating coil. During vaping, the controller 48 controls a supply of electrical power from the power supply 50 to the electric heater 64. The heater section 26 further comprises a liquid transfer element 62 in the form of a capillary wick. The resistive heating coil is wound around a first portion of the liquid transfer element 62.

The electric heater 64 and the liquid transfer element 62 are supported by a piercing element extending from an upstream end wall of the cavity 26. The piercing element comprises a hollow shaft portion 232 and a piercing portion 234. The electric heater 64 and the first portion of the liquid transfer element 62 are positioned in an airflow passage formed within the hollow shaft portion 232. Second and third portions of the liquid transfer element 62 extend through apertures in the hollow shaft portion 232. The second and third portions are folded at about a 90 degree angle so that they overlie an outer surface of the hollow shaft portion 232.

FIG. 6 is a cross-sectional view of the aerosol-generating system 200 after the cartridge 218 has been inserted into the cavity 26 of the aerosol-generating device 212. When the cartridge 218 is inserted into the cavity 26 the piercing portion 234 of the piercing element pierces the first and second. frangible seals 248, 250. The heater section 263 is received within the passage 254 defined through the porous carrier material 260 so that the second and third portions of the liquid transfer element 62 contact the inner surface of the porous carrier material 260. The liquid aerosol-forming substrate 58 is wicked along the liquid transfer element 62 to the electric heater 64.

Vaping of the aerosol-generating system 200 is substantially identical to vaping of the aerosol-generating system 10 described with reference to FIGS. 1 to 3. That is, when the cartridge 218 is not received within the cavity 26, air flows into the cavity 26 via the bypass air inlet 19 when a vaper draws on the downstream end of the aerosol-generating device 212. When a vaper draws on the downstream end of the aerosol-generating system 200 with the cartridge 218 received within the cavity 26, airflow enters the aerosol-generating system 200 via the airflow inlet 46 and flows across the airflow sensor 51 to activate the aerosol-generating system 200.

FIG. 7 is an illustration of at least one example embodiment of a heater section 363 for the aerosol-generating system 200 of FIGS. 5 and 6. The heater section 363 is similar in construction to the heater section 263 described with reference to FIGS. 5 and 6 and like reference numerals are used to designate like parts.

The heater section 363 differs from the heater section 263 by the addition of a securing ring 367 positioned about the upstream end of the hollow shaft portion 232. The ends of the second and third portions 363, 365 of the liquid transfer element 62 are secured between the securing ring 367 and the hollow shaft portion 232 to retain the liquid transfer element 62 in the correct position during insertion and removal of the heater section 363 into and from the passage 254 defined through the porous carrier material 260.

While a number of example embodiments have been disclosed herein, it should be understood that other variations may be possible. Such variations are not to be regarded as a departure from the spirit and scope of the present disclosure, and all such modifications as would be obvious to one skilled in the art are intended to be included within the scope of the following claims.

We claim:

1. An aerosol-generating system comprising;
- a cartridge including,
  - a cartridge housing, and
  - a solid aerosol-forming substrate in the cartridge housing;
- a liquid aerosol-forming substrate; and
- an aerosol-generating device including,
  - a cavity configured to receive at least a portion of the cartridge,
  - an airflow inlet,
  - an airflow sensor between the airflow inlet and the cavity, the airflow sensor in fluid communication with the airflow inlet and the cavity,
  - a bypass air inlet in fluid communication with the cavity,
  - an electric heater configured to heat the liquid aerosol-forming substrate,
  - a power supply configured to supply power to the electric heater, and
  - a controller configured to control a supply of electrical power from the power supply to the electric heater in response to a signal from the airflow sensor indicative of airflow across the airflow sensor,
- the aerosol-generating system configured such that the cartridge housing substantially prevents airflow through the bypass air inlet when the cartridge is received within the cavity.

2. The aerosol-generating system according to claim 1, wherein the bypass pair inlet is in a sidewall of the cavity.

3. The aerosol-generating system according to claim 1, wherein the bypass air inlet comprises a plurality of bypass air inlets, and the aerosol-generating system is configured such that the cartridge housing substantially prevents airflow through each of the bypass air inlets when the cartridge is within the cavity.

4. The aerosol-generating system according to claim 1, wherein the aerosol-generating device comprises a liquid storage section and the liquid aerosol-forming substrate is positioned within the liquid storage section.

5. The aerosol-generating system according to claim 4, wherein the liquid storage section comprises a porous carrier material, and the liquid aerosol-forming substrate is on the porous carrier material.

6. The aerosol-generating system according to claim 1, wherein the aerosol-generating device further comprises a liquid transfer element configured to transfer the liquid aerosol-forming substrate to the electric heater.

7. The aerosol-generating system according to claim 1, wherein the liquid aerosol-forming substrate is within the cartridge housing.

8. The aerosol-generating system according to claim 7, wherein the cartridge comprises a porous carrier material, and the liquid aerosol-forming substrate is on the porous carrier material.

9. The aerosol-generating system according to claim 8, wherein the aerosol-generating device comprises a liquid transfer element configured to transfer the liquid aerosol-forming substrate from the porous carrier material to the electric heater.

10. The aerosol-generating system according to claim 9, wherein the cartridge further comprises a frangible seal, and the aerosol-generating device further comprises a piercing element configured to pierce the frangible seal when the cartridge is inserted into the aerosol-generating device.

11. The aerosol-generating system according to claim 10, wherein the piercing element comprises:
   a hollow shaft portion; and
   a piercing portion at an end of the hollow shaft portion, at least a portion of the electric heater being positioned inside the hollow shaft portion.

12. The aerosol-generating system according to claim 11, wherein a first portion of the liquid transfer element is inside the hollow shaft portion, and the electric heater comprises a resistive heating coil at least partially wound around the first portion of the liquid transfer element.

13. The aerosol-generating system according to claim 12, wherein the liquid transfer element extends through an aperture in the hollow shaft portion, and a second portion of the liquid transfer element overlies an outer surface of the hollow shaft portion.

14. The aerosol-generating system according to claim 13, wherein the porous carrier material has an annular shape, the porous carrier material defining a passage therein, the aerosol-generating system being configured such that the piercing element is at least partially received within the passage when the aerosol-generating device receives the cartridge, and the aerosol-generating system being configured such that the second portion of the liquid transfer element contacts an inner surface of the porous carrier material when the piercing portion is at least partially received within the passage.

15. The aerosol-generating system according to claim 14, wherein the cartridge further comprises an airflow channel between the porous carrier material and the cartridge housing, and a downstream end of the airflow channel is in fluid communication with the solid aerosol-forming substrate.

* * * * *